(12) United States Patent
Franciskovich et al.

(10) Patent No.: US 9,017,994 B2
(45) Date of Patent: Apr. 28, 2015

(54) TEST PACK TO MONITOR EFFECTIVENESS OF STERILIZATION PROCESS

(75) Inventors: Phillip P. Franciskovich, Concord, OH (US); Tricia A. Cregger, Fairlawn, OH (US)

(73) Assignee: American Sterilizer Company, Mentor, OH (US)

( * ) Notice: Subject to any disclaimer, the term of this patent is extended or adjusted under 35 U.S.C. 154(b) by 317 days.

(21) Appl. No.: 13/270,491

(22) Filed: Oct. 11, 2011

(65) Prior Publication Data

US 2013/0089922 A1  Apr. 11, 2013

(51) Int. Cl.
*A61L 2/28* (2006.01)
*C12Q 1/22* (2006.01)

(52) U.S. Cl.
CPC .... *A61L 2/28* (2013.01); *C12Q 1/22* (2013.01)

(58) Field of Classification Search
CPC ..................................... C12Q 1/22; A61L 2/28
USPC ......................................... 435/287.4; 422/417
See application file for complete search history.

(56) References Cited

U.S. PATENT DOCUMENTS

| | | | |
|---|---|---|---|
| 3,752,743 | A | 8/1973 | Henshilwood |
| 5,552,320 | A | 9/1996 | Smith |
| 5,870,885 | A | 2/1999 | Biddle et al. |
| 5,872,004 | A | 2/1999 | Bolsen |
| 6,355,448 | B1 | 3/2002 | Foltz et al. |
| 6,897,059 | B2 | 5/2005 | Foltz et al. |
| 7,045,343 | B2 | 5/2006 | Witcher et al. |
| 7,927,866 | B2 | 4/2011 | Justi et al. |

FOREIGN PATENT DOCUMENTS

| | | | |
|---|---|---|---|
| EP | 058019 | 8/1982 | |
| EP | 0 416 504 | * 3/1991 | ............... A61L 2/26 |
| EP | 0421760 | 4/1991 | |
| EP | 1704872 | 9/2006 | |
| WO | 2008130802 | 10/2008 | |
| WO | 2010045138 | 4/2010 | |

OTHER PUBLICATIONS

PCT/US2012/058685; PCT International Search Report and Written Opinion of the International Searching Authority dated Jan. 10, 2013.
Website page for 3M Attest Rapid 5 Steam Plus Test Pack 41382F; Jan. 9, 2012.
Website page for 3M Attest Biological Indicators and Test Packs for Ethylene Oxide; Jan. 10, 2012.

* cited by examiner

*Primary Examiner* — Nathan Bowers
*Assistant Examiner* — Gautam Prakash
(74) *Attorney, Agent, or Firm* — Renner, Otto, Boisselle & Sklar, LLP

(57) ABSTRACT

A sterilization test pack, including a base comprising a pair of recessed compartments, wherein the recessed compartments are arranged in a non-concentric relationship and are in fluid communication with each other; a cover attached to the base and forming a sealed enclosure for the recessed compartments; an external channel providing the only fluid communication between the sealed enclosure and an external environment; a selected sterilization indicator in a first of the recessed compartments; and a chemical integrator and/or a chemical indicator in a second of the recessed compartments, in which the external channel is configured to allow only restricted flow of a gaseous sterilization medium into the recessed compartments and the base and cover are otherwise impenetrable by the gaseous sterilization medium.

18 Claims, 3 Drawing Sheets

TEST PACK TO MONITOR EFFECTIVENESS OF STERILIZATION PROCESS

BACKGROUND

1. Field of the Invention

This invention relates to the field of sterilization processes and in particular to indicators for sterilization cycles.

2. Description of Prior Art

In the field of cleaning, disinfection and sterilization of articles, it is desirable to determine whether a particular load of articles that is subjected to a sterilizing environment (i.e., gases such as steam, hydrogen peroxide or ethylene oxide or other environments such as a plasma) has, in fact, been exposed to an environment which should have killed the microorganisms sought to be killed. For example, U.S. Pat. No. 7,186,374 issued Mar. 6, 2007, the disclosure of which is incorporated herein by reference, discloses a method of sterilizing using vaporized hydrogen peroxide as the sterilant. It is desirable to have a simple, quick test to determine whether the sterilization environment reached the more secluded areas of the objects placed within the sterilizer.

One way of testing is to use a biological indicator as shown, for example, by U.S. Pat. No. 5,872,004 to Bolsen. Biological indicators contain a calibrated population of living organisms, e.g. bacterial spores, having a high resistance to the sterilization process under investigation. The indicator is inserted into the test chamber with the load and exposed to the sterilizing environment for the sterilizing cycle. After exposure to the sterilization cycle, the indicator is incubated in a nutrient media to encourage outgrowth of any remaining viable spores. Growth of microorganisms is an indication that the sterilization process has not been effective. U.S. Pat. Nos. 5,872,004 and 7,927,866 disclose disposable biological test packs.

Known test packs, while effective, are generally complex and costly to manufacture, requiring many parts, and can be difficult to use.

SUMMARY

The present invention relates to a sterilization test pack, including:
- a base comprising a pair of recessed compartments, in which the recessed compartments are arranged in a non-concentric relationship and are in fluid communication with each other;
- a cover attached to the base and forming a sealed enclosure for the recessed compartments;
- an external channel providing the only fluid communication between the sealed enclosure and the external environment;
- a sterilization indicator in a first of the recessed compartments; and
- a chemical integrator and/or a chemical indicator in a second of the recessed compartments,
- in which the external channel is configured to allow only restricted flow of a gaseous sterilization medium into the recessed compartments and the base and cover are otherwise impenetrable by the gaseous sterilization medium.

In one embodiment, the test pack is free of a sterilant absorber positioned within the sealed enclosure.

In one embodiment, the recessed compartments are in a substantially parallel side by side relationship.

In one embodiment, the test pack includes a single external channel, in which the one external channel is in direct fluid communication with only the first of the recessed compartments, and the first recessed compartment is in fluid connection with a second of the recessed compartments via an internal channel.

In one embodiment, the test pack includes two external channels, in which a first of the two external channels is in fluid communication with the first of the recessed compartments, and a second of the two external channels is in fluid communication with a second of the recessed compartments. In one embodiment, even though there are two external channels, the first and second recessed compartments are in fluid communication with each other via the internal channel.

In one embodiment, the external channel, or each external channel, has no bends between the sealed enclosure and the external environment, i.e., it is a straight channel. In one embodiment, the external channel, or each external channel, has at least one bend between the sealed enclosure and the external environment. In another embodiment, the external channel, or each external channel has a plurality of bends between the sealed enclosure and the external environment.

In one embodiment, each external channel independently has a depth in the range from about 0.025 mm to about 4 mm and a width in the range from about 0.025 mm to about 5 mm, and a length in the range from about 1 mm to about 100 mm.

In one embodiment, the depth and width of each external channel are selected to provide the restricted flow of the gaseous sterilization medium appropriate for the selected sterilization indicator.

In any of the foregoing embodiments, the sterilization indicator may include at least one of a biological indicator and an indicator enzyme.

In any of the foregoing embodiments, at least one of the base or the cover may be sufficiently transparent that the chemical indicator is visible after the sterilization test pack has been exposed to the sterilization medium.

In any of the foregoing embodiments, the base may include one or a combination of two or more of polycarbonate, polyolefin, polystyrene, polyacrylamide, polymethacrylate, poly (methyl)methacrylate, polyimide, polyester, polyethylene terephthalate, polybutylene terephthalate and polyvinylchloride.

In any of the foregoing embodiments, the cover may include one or a combination of two or more of mylar, metal foil, polyester, polyolefin, polycarbonate, polyolefin, polystyrene, polyacrylamide, polymethacrylate, poly(methyl) methacrylate, polyimide, polyester, polyethylene terephthalate, polybutylene terephthalate, polyvinylchloride, a metallized polymer film using any of the foregoing polymers, and cardboard.

In any of the foregoing embodiments, the cover may be sealed to the base by one or a combination of two or more of heat, adhesive, heat-activated laminate adhesion, sonic welding and magnetic induction.

In any of the foregoing embodiments, the base may include a substantially flat raised surface to which the cover is sealed.

In any of the foregoing embodiments, the test pack may have one external channel and two recessed compartments, and the two recessed compartments may be in fluid communication with each other.

In any of the foregoing embodiments, each external channel independently may be an S-shape channel having two bends, or may have no bends, a single bend or more than two bends.

In any of the foregoing embodiments, the sterilization indicator may include a biological indicator and/or an indicator enzyme.

The sterilization test packs in accordance with the present invention combine one or more of the following attributes, which address and provide a solution to problems in the prior art: the test packs are effective, are simple and easy to manufacture, require few parts, and are quite easy to use.

BRIEF DESCRIPTION OF THE DRAWINGS

Various embodiments of the present invention are described in the following with references to the accompanying drawings, in which.

Figure 1:
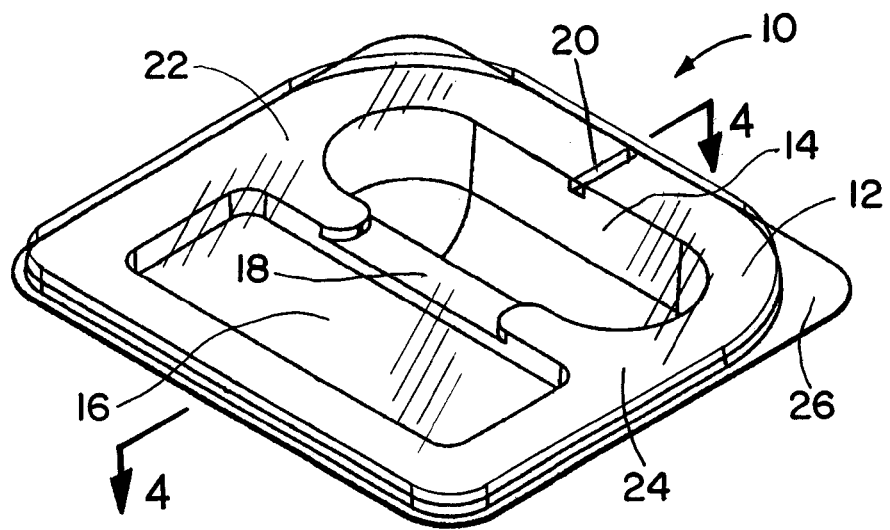
FIG. 1 is a side-top perspective view of a test pack in accordance with an embodiment of the invention.

It should be appreciated that for simplicity and clarity of illustration, elements shown in the Figures have not necessarily been drawn to scale. For example, the dimensions of some of the elements may be exaggerated relative to each other for clarity. Further, where appropriate, reference numerals have been repeated among the Figures to indicate corresponding elements.

DETAILED DESCRIPTION

The present invention includes a test pack that functions comparably to the configuration that it is intended to replace and yet is easy to manufacture, requires fewer parts than most currently marketed test packs and is easy for the customer to use. It also enables a manufacturer to alter the timing of the test pack by simply changing the number, size, positioning and shape of the channels to allow for more applications in the future.

The term "sterilization" may refer to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term sterilization may be used herein to also refer to methods and procedures less rigorous than sterilization, for example, disinfection, sanitization, and the like. The sterilization test pack and the processes and apparatus described herein may be used in health care fields, scientific fields, and the like. These may be used in commercial and industrial applications where sterilization, disinfection, sanitization, and the like, may be desired, for example, food processing, pharmaceutical manufacturing, and the like.

The sterilization process for which the disclosed sterilization test pack may be used may be any gaseous sterilization process. These may include sterilization processes wherein the sterilization medium or sterilant may be steam or one or more gaseous sterilants, and the like. The gaseous sterilants may comprise gaseous hydrogen peroxide, gaseous ethylene oxide, and the like.

The biological indicator in the present test pack may be used to determine the lethality of sterilants against any microorganism with less resistance to the sterilization process than the test organism provided with the biological indicator. These microorganisms may include bacteria such as *Escherichia coli, Legionella* sp., *Campylobacter* sp., and other enteric bacteria, as well as *Staphylococcus* and *Streptococcus* species and other human pathogenic microorganisms such as *Cryptosporidium*.

The biological indicator in the present test pack may comprise one or more test organisms. The test organism may comprise any cell whose resistance to the intended sterilization process exceeds that of the other organisms which the sterilization process is designed to destroy. The type of test organism used as the biological indicator may be dependent upon a variety of factors exemplified by, but not limited to, the type of sterilization process being used. The test organism may be a microorganism. The strains that may be used may be those that are the most resistant to the process used for sterilization. The test microorganism may comprise bacteria. The bacterial microorganisms may be those which form endospores, i.e., bacterial spores. The test organism may comprise bacteria of the *Geobacillus, Bacillus* or *Clostridia* genera. These may include *Geobacillus stearothermophilus, Bacillus atrophaeus, Bacillus subtilis, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans*, or a mixture of two or more thereof.

The indicator organism of the biological indicator may comprise fungi, mycobacteria, protozoa, vegetative bacteria, vegetative cells and/or their constituent parts and the like. Examples of fungi that may be used may include *Aspergillus niger, Candida albicans, Trichophyton mentagrophytes, Wangiella dermatitis*, and the like. Examples of mycobacteria that may be used may include *Mycobacterium chelonae, Mycobacterium gordonae, Mycobacterium smegmatis, Mycobacterium terrae*, and the like. Examples of protozoa that may be used may include *Giardia lamblia, Cryptosporidium parvum*, and the like. Examples of vegetative bacteria that may be used may include *Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, and the like. Organisms such as *Geobacillus stearothermophilus, Bacillus atrophaeus, Bacillus subtilis, Bacillus coagulans, Clostridium sporogenes*, and the like, may be used for determining the efficacy of moist heat sterilization (autoclaving), with *Geobacillus stearothermophilus* being especially useful.

In one embodiment, the test organism comprises *Aspergillus niger, Candida albicans, Trichophyton mentagrophytes, Wangiella dermatitis, Mycobacterium chelonae, Mycobacterium gordonae, Mycobacterium smegmatis, Mycobacterium terrae, Mycobacterium bovis, Mycobacterium tuberculosis, Giardia lamblia, Cryptosporidium parvum, Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Micrococcus radiodurans, Deinococcus radiodurans, Staphylococcus aureus, Staphylococcus epidermidis, Stenotrophomonas maltophilia*, or a mixture of two or more thereof.

In addition to the test organisms selected on the basis of their acceptance as representing the most resistant organism (e.g. *Geobacillus stearothermophilus* and *Bacillus atropheaus*), the biological indicator may further comprise agents of bioterrorism or biowarfare, e.g., *Bacillus anthracis* and the like. These resistant organisms may also comprise strains which have become resistant to formerly effective means of antibiotic treatment or chemical disinfection due to natural or man-made modifications. Examples of the former type may include VREs (Vancomycin Resistant *enterococci*), MSRAs (Methicillin Resistant *Staphylococcus aureus*), *Mycobacterium cheloni*, and the like. Such resistant organisms may be desirable because the VREs and MRSAs have recently developed resistance to therapeutic countermeasures (e.g., antibiotic resistance) and *M. cheloni* has developed resistance to some modes of disinfection (e.g., glutaraldehyde resistance).

The indicator enzyme may comprise beta-D-galactosidase, alpha-D-galactosidase, beta-D-glucosidase, alpha-D-glucosidase, beta-D-cellobiosidase, alpha-L-Arabinosidase, alpha-mannosidase, alpha-galactosaminidase, beta-galactosaminidase, beta-gluconidase, beta-xylosidase, beta-D-glucuronidase, beta-D-fucosidase, beta-L-fucosidase, alpha-glucosaminidase, beta-glucosaminidase, beta-lactosidase, alpha-maltosidase, alpha-mannosidase, beta-mannosidase, alkaline phosphatase, acid phosphatase, carboxyl esterase, butyrate esterase, caprylate esterase lipase, chloramphenicol acetytransferase, catechol-2,3-dioxygenase, myristate lipase, leucine aminopeptidase, valine aminopeptidase, phosphohydrolase, alpha-L-arabinofuranosidase, N-acetyl-beta-glucosaminidase, alanine aminopeptidase, proline aminopeptidase, tyrosine aminopeptidase, phenylalanine aminopeptidase, fatty acid esterase, or a mixture of two or more thereof.

Referring now to FIGS. 1-5, test packs in accordance with embodiments of the present invention are depicted.

FIG. 1 is a side-top perspective view of a test pack in accordance with an embodiment of the invention. As shown in FIG. 1, the test pack 10 in this embodiment has a base 12 in the form of a bottom tray made of a moldable or thermoformable material such as one or a combination of two or more of polycarbonate, polyolefin (e.g., polypropylene), polystyrene, polyacrylamide, polymethacrylate, poly(methyl)methacrylate, polyimide, polyester, polyethylene terephthalate, polybutylene terephthalate and polyvinylchloride. In one embodiment, a polypropylene is used for the base, such as MARLEX® RGX-020 polypropylene random copolymer. The base 12 is formed with a pair of recessed compartments 14 and 16. As shown in the embodiment of FIG. 1, the recessed compartments 14, 16 are arranged in a non-concentric relationship and are in fluid communication with each other via an internal channel 18. The internal channel 18 provides fluid communication between the pair of recessed compartments 14, 16.

The base 12 of the test pack may be made by any suitable process, but it is expected that the most desirable is for the base to be thermoformed.

In accordance with the present invention, the test pack 10 includes an external channel 20 which provides fluid communication with the external environment. As described with respect to other embodiments, the test pack may include more than one external channel. The external channel 20, and any additional external channel(s), are configured and of a size to allow only restricted flow of the external atmosphere, such as a gaseous sterilization medium, into the recessed compartments 14, 16 of the test pack 10. The external channel may be thermoformed or cut into the base, as appropriate.

The test pack 10 further includes a cover 22 attached to the base 12 and forming a sealed enclosure for the recessed compartments 14, 16. The cover 22 may be a peelable, clear material, as described in more detail below. The cover 22 is removably sealed to the base 12 using, e.g., an adhesive, and provides a complete seal between the internal spaces within the test pack, e.g., the recessed compartments, and the external environment, with the only opening(s) in the test pack 10 being the external channel(s) 20. The cover 22 provides the top to the external channel 20, thus closing the channel on all sides, leaving only the outer and inner ends of the channel open.

As shown in FIG. 1, in this embodiment, the base 12 includes a flat, raised surface 24 and one or more lower tab(s) 26. The cover 22 is adhesively but removably attached to the raised surface 24, but does not extend to the tab(s) 26. The tab(s) 26 are provided, for example, for handling the test pack 10, and are useful for grasping the base 12 when removing the cover 22.

The cover 22 may be made of a clear plastic film or foil. Although a clear polyester such as PET is preferred, polycarbonate, polyethylene, polypropylene, polystyrene, PVC, acrylic plastics, nylon or an opaque aluminum foil may be used. In one embodiment, the cover comprises one or a combination of two or more of mylar, metal foil, metallized foil, polyester, polyolefin, polycarbonate, polystyrene, polyacrylamide, polymethacrylate, poly(methyl)methacrylate, polyimide, polyester, polyethylene terephthalate, polybutylene terephthalate, polyvinylchloride and cardboard.

In one embodiment, the cover 22 is made of an autoclaveable polymer, and in one embodiment is made of an autoclaveable polyester foil peelable laminate, such as TOLAS™ ITD-6121 laminate. In one embodiment, the laminate includes multiple layers, and may include a layer of polyester, a layer of foil and a layer of a sealant film, each sandwiched and held together by intervening adhesive layers. Thus, in one embodiment, an outer layer of the cover 22 comprises PET, and the inner layer of the cover 22 comprises a HDPE coextruded sealant film, with a thin layer of foil, e.g., aluminum, sandwiched between the outer and inner layers. In the assembled test pack, the sealant film would be bonded to the raised surface 24 of the base 12.

It is desirable that the chemical indicator be visible from outside the test pack, so that it is readily determinable if the test pack has been exposed to the sterilization medium to which the chemical indicator is sensitive.

In one embodiment, if the cover 22 is not clear, the base 12 is made of a clear plastic material, to facilitate viewing of the chemical integrator and indicator without the necessity of opening the test pack. The cover 22 is held in place by a suitable adhesive, which removably seals the cover 22 to the base 12. The cover 22 may be left partially without adhesive near one corner portion to permit ease of grasping the cover 22 to remove it from the base 12, to provide access to the indicators. In another embodiment (not shown), the cover 22 may extend outward over an edge of the base 12, to facilitate grasping the cover 22 for removal.

The cover 22 may be attached to the base 12 by any suitable means, including but not limited to, heat seal, adhesive, sonic weld or magnetic induction seal. The seal of the cover 22 to the base 12 is such that following the processing of the test pack in the sterilization process, the cover 22 remains securely attached to the base 12 even in a sterilization such as steam sterilization in an autoclave, but can be purposefully pulled away to enable access to the biological indicator and the chemical indicator or integrator.

In the embodiment shown in FIG. 1, the external channel 20 is formed in the base 12 and is a single, straight channel. When the cover 22 is in place, the external channel 20 provides the only communication between the inner recessed compartments 14, 16 and the external environment, such as a sterilization atmosphere, outside of the test pack 10.

In one embodiment, the test pack 10 contains a biological indicator, such as a self-contained biological indicator (SCBI) in the first recessed compartment 14. In one embodiment, the test pack 10 contains a chemical integrator or a chemical indicator in the second recessed compartment 16.

Figure 2:
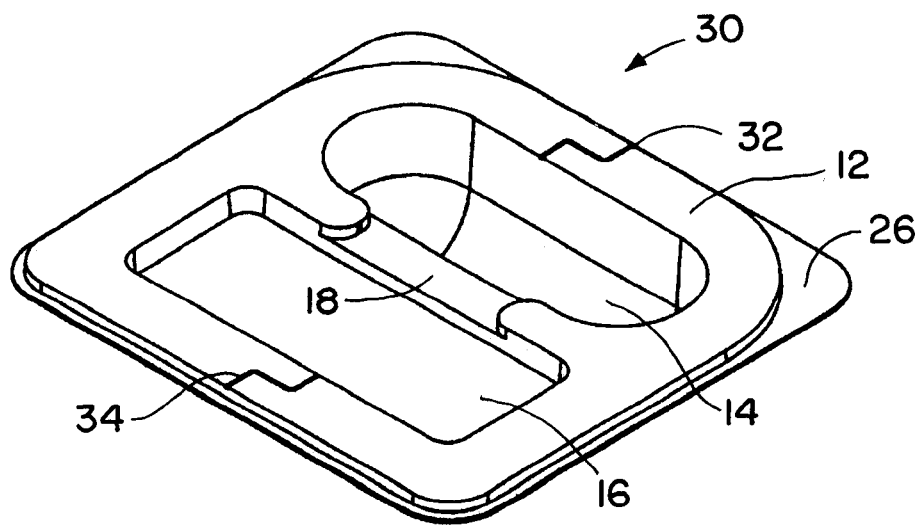
FIG. 2 is a side-top perspective view of a base of a test pack in accordance with another embodiment of the invention.
Figure 6:
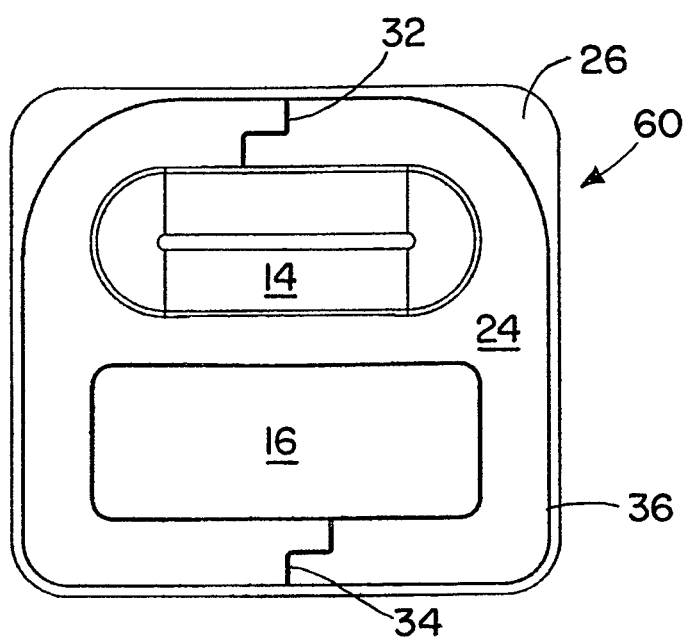
FIG. 6 is a top plan view of a test pack in accordance with another embodiment of the present invention.

Another embodiment in accordance with the present invention is shown in FIG. 2, which is also a side-top perspective view of a base 12 of a test pack 30. The test pack 30 is substantially similar to the test pack 10 except that the test pack 30 includes two external channels 32, 34 and each of the external channels 32, 34 includes two bends. In this embodiment, the external channel 32 provides fluid communication between the first recessed compartment 14 and the external environment, and the external channel 34 provides fluid communication between the second recessed compartment 16 and the external environment. In the embodiment shown in FIG. 2, the internal channel 18 again provides fluid communication between the recessed compartments 14, 16. In one embodiment, net shown in FIG. 6, in the test pack 60, there are two external channels 32, 34, providing fluid communication between the recessed compartments 14, 16, respectively, and the external environment, but the internal channel is absent, i.e., there is no fluid communication directly between the recessed compartments 14, 16. In the embodiments of FIG. 2 and FIG. 6, the sealable cover is not shown.

Figure 3:
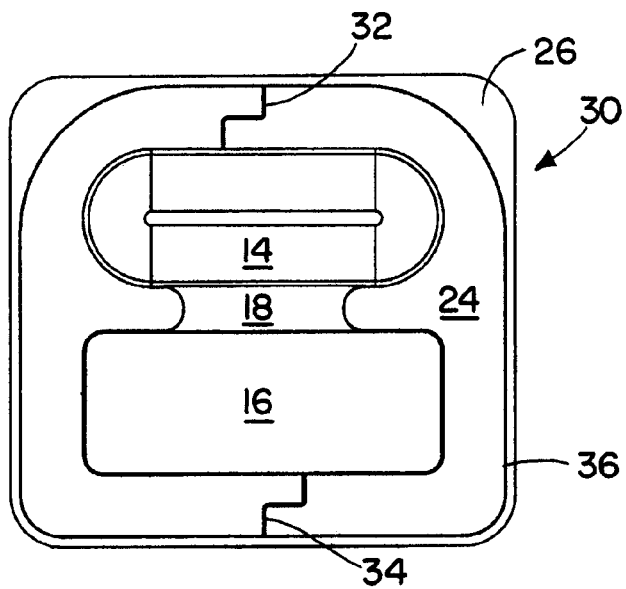
FIG. 3 is a top plan view of the test pack embodiment of FIG. 2.

FIG. 3 is a top plan view of a test pack embodiment 30 similar to that of FIG. 2, which more clearly shows that the base 12 includes a narrow peripheral lip 36 around the periphery of the base, which expands into the tabs 26 at two adjacent corners of the base 12, in this embodiment. Although not shown, in other embodiments, the tab 26 may be omitted, or a single tab 26 may be used, or the tabs 26 may be on opposite corners or on three or even all four corners of the base 12. FIG. 3 shows the raised surface 24 to which the cover 22 is adhered, and the peripheral lip 36, and the two external channels 32, 34.

Figure 4:
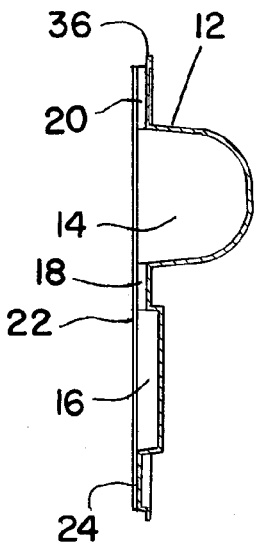
FIG. 4 is a cross-sectional view along lines 4-4 of FIG. 1.

FIG. 4 is a cross-sectional view along lines 4-4 of FIG. 1, showing the base 12. As shown in FIG. 4, the raised surface 24 is slightly raised relative to the peripheral lip 36, and the first recessed compartment 14 is considerably deeper than is the second recessed compartment 16, in this embodiment. That is because, in this embodiment, a sterilization indicator such as a SCBI, which occupies a substantial three-dimensional volume, will be disposed in the first recessed compartment 14, while a relatively flat chemical integrator or chemical indicator will be disposed in the second recessed compartment 16.

Figure 5:
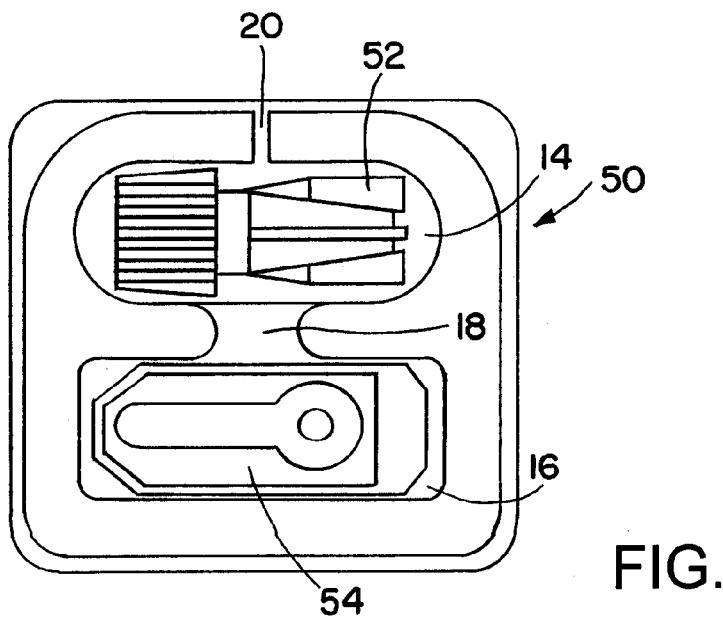
FIG. 5 is a top plan view of a test pack in accordance with an embodiment of the present invention, with a biological indicator in a first recessed compartment and a chemical indicator in a second recessed compartment.

FIG. 5 is a top plan view of a test pack 50 in accordance with an embodiment of the present invention, with a biological indicator 52 in a first recessed compartment 14 and a chemical indicator 54 in a second recessed compartment 16. In the embodiment of FIG. 5, the biological indicator is depicted as a SCBI, but any suitable biological indicator can be used. In the embodiment of FIG. 5, the chemical indicator is shown, but a chemical integrator may be used instead. In one embodiment, not shown, both a chemical indicator and a chemical integrator may be used.

In one embodiment, the base 12 is thermoformed and receives a chemical indicator and a biological indicator. The peelable cover 22 is then sealed to the raised surface 24 of the base 12 so the only communication between the recessed compartments 14, 16 and the external environment is through the external channels, e.g., the external channel 20 or the two external channels 32, 34.

In use, the test pack 10, 30, 50 of the present invention is placed within the chamber of a sterilizer along with the objects to be sterilized. The exact location at which the test pack is placed within the sterilization chamber may be suitably determined by the skilled person.

The external channels are sized so as to restrict flow of the sterilization medium into the test pack. Adjusting the dimensions of the external channel or channels, and/or changing the number of external channels will permit more or less of the gaseous sterilization medium to enter the external channel(s) and penetrate the test pack. In one embodiment, each external channel independently has a depth in the range from about 0.025 mm to about 4 mm and a width in the range from about 0.025 mm to about 5 mm, and a length in the range from about 1 mm to about 25 mm. In one embodiment, the depth is in the range from about 0.05 to about 2 mm, and in another embodiment the depth is in the range from about 0.25 to about 3 mm, and in one embodiment, the depth is about 1.27 mm. In one embodiment, the width is in the range from about 0.05 to about 2 mm, in another embodiment the width is in the range from about 0.025 to about 0.25 mm and in another embodiment the width is in the range from about 0.025 to about 1 mm, and in one embodiment, the width is about 1.27 mm. In one embodiment, the length of the channel ranges from about 3 mm to about 30 mm, and in another embodiment the length is in the range from about 5 mm to about 15 mm, and in another embodiment, the length is in the range from about 8 mm to about 10 mm. In one embodiment, the depth and width both are about 1.27 mm and the length is about 7.9 mm to about 9.55 mm. All of the foregoing lengths encompass the entire length of the channel, including bends and the distance between any bends present.

Any suitable combination of the foregoing depths, widths and lengths may be selected and is considered to be within the scope of the present disclosure and directly derivable therefrom by the skilled person. Any suitable combination of depth, width and length may be selected, with or without the introduction of bends, as needed to obtain the desired restricted flow of gaseous sterilant into the recessed compartments 14, 16 of the test pack disclosed herein. As will be understood, introduction of bends allows the total length of the channel to be increased, without necessarily increasing the width of the raised surface 24.

In one embodiment, the size of the channel can be expressed as a cross-sectional area of the channel. For example, the cross-sectional area of the channel having depth and width about 1.27 mm, would be about 1.6 $mm^2$. In one embodiment, the cross-sectional area of the channel may be in the range from about 0.05 $mm^2$ to about 5 $mm^2$.

In one embodiment, the size of the channel can be expressed as a volume of the channel. For example, the volume of the channel having depth and width about 1.27 mm and length from about 7.9 mm to about 9.55 mm, would be in the range from about 12.7 $mm^3$ to about 15.4 $mm^3$. In one embodiment, the volume of the channel may be in the range from about 1 $mm^3$ to about 125 $mm^3$.

Some amount of adjustment may be required to obtain an optimum channel dimension and shape, depending on factors known to the skilled person, including the organism(s) in the biological indicator and the sterilization medium and conditions in which the test pack is intended to be used.

Here, and elsewhere in the present disclosure, the numerical limits of the range and ratio limitations can be combined. Thus, for example, in the foregoing, although not specifically enumerated, a depth in the range from about 0.05 to about 1 mm is included within the specifically disclosed ranges. The depth and width of the external channel may be selected to provide the restricted flow of the gaseous sterilization medium appropriate for the selected sterilization indicator and for the gaseous sterilization medium used.

During operation of the sterilizer, a portion of the gaseous sterilization medium enters the recessed compartments 14, 16 through the external channel 20 or 32 and, when present, 34, and any additional external channels that may be present in other embodiments. As the sterilization process continues, the gaseous sterilization medium permeates into the chemical indicator or integrator, causing the chemical indicator or integrator to indicate it has been in contact with a sufficient quantity of the gaseous sterilization medium for a sufficient time. As the sterilization process continues, a portion of the gaseous sterilization medium permeates into the biological indicator and, when sufficient exposure (time, temperature, gaseous sterilant concentration, etc.) has been attained, the sterilization process is terminated. In accordance with the present invention, the operator of the process can quickly and easily see whether the chemical indicator or integrator has changed color or otherwise indicated sufficient exposure to the sterilization medium. Upon observation of this initial confirmation, the operator can remove the test pack from the sterilization apparatus, and then open the test pack by peeling back the cover to remove the biological indicator for incubation and/or further testing to confirm the efficacy of the sterilization process. The remains of the test pack can then be discarded or recycled, as appropriate.

In accordance with an embodiment of the present invention, the test pack is free of a sterilant absorber positioned within the sealed enclosure. That is, in this embodiment, due to the restricted flow of gaseous sterilization medium allowed to pass through the external channel(s), it is not necessary to provide any sort of absorber or similar sterilant-reactive device to inhibit or reduce flow of the gaseous sterilization medium into the recessed chambers of the test pack of the present invention. In the prior art, such absorbers were commonly required, but are not needed with embodiments of the present invention. In accordance with the present invention, the external channel or channels provide all the inhibition of sterilant flow into the test pack needed to most closely simulate worst case sterilization conditions to which the remainder of the load would be exposed. This restriction of flow of sterilant helps to provide an accurate indication of whether sufficient sterilant has reached both any microorganisms in the load and the biological indicator to approximately equivalent degrees. As will be readily understood, if sterilant more easily reaches the indicator than reaches the load to be sterilized, the biological indicator may yield a false negative result, which is obviously undesirable. On the other hand, if the sterilant equally or less easily reaches the indicators, then a negative result would be a true indication of the successful sterilization of the load, which is desirable. Thus, the test pack of the present invention provides an initial indication of completed sterilization cycle via the chemical indicator. The biological indicator is then used to determine whether sufficient sterilization atmosphere was provided for sufficient time to cause sterilization.

EXAMPLES

Two configurations of this test pack design are tested alongside a 16-towel test pack in various autoclave cycles. The configurations include "straight" channels and "s-shaped" channels, both configurations are thermally molded using polypropylene. The straight channel has depth, width and length dimensions 1.3 mm×1.3 mm×8 mm, and is substantially straight, i.e., without bends. The S-shaped channel has depth and width dimensions 0.38 mm×0.25 mm×15.4 mm, and includes two approximately 90° bends intermediate the length of the channel. The peel-away foil used is TOLAS™ ITD 6121 polyester laminate including a heat-sealable film as a bottom layer, sealed using a heat-seal method. The results of both the biological indicator and the chemical integrator when processed in a STERIS® CENTURY® SV-120 sterilizer are shown in Table 1. Results of test packs made with a single straight channel having the same size and shape as noted above and processed in a STERIS® CENTURY® SV-116 sterilizer are shown in Table 2. It is important to note that the present invention performed comparably to the standard 16-towel pack as required. "BI" is biological indicator; "Integrator" is a VERIFY® Integrating Indicator (a chemical integrator) for steam sterilization.

TABLE 1

Results of Test Pack Performance in SV-120

| | Test Pack | | | | | |
|---|---|---|---|---|---|---|
| | 2-Straight Channel | | 2-S-Shaped Channel | | 16-Towel Pack | |
| Cycle | BI | Integrator | BI | Integrator | BI | Integrator |
| Complete Pre-vac, 132° C., 4 min. | Pass | Pass | Pass | Pass | Pass | Pass |
| Abort Pre-vac, 132° C., 1 pulse | Fail | Fail | Fail | Fail | Fail | Fail |
| Abort Pre-vac, 132° C., 4 pulse | Fail | Fail | Fail | Fail | Fail | Fail |
| Complete Gravity, 121° C., 30 min. | Pass | Pass | Pass | Pass | Pass | Pass |
| Abort Gravity, sterilize time = 0 min | Fail | Fail | Fail | Fail | Fail | Fail |
| Abort Gravity, sterilize time = 10 min | Fail | Fail | Fail | Fail | Fail | Fail |
| Abort Gravity, sterilize time = 15 min | Fail | Fail | Fail | Fail | Fail | Fail |

TABLE 2

Results of Test Pack Performance with 1-Straight Channel in SV-116

| | Test Pack | | | |
|---|---|---|---|---|
| | 1-Straight Channel | | 16-Towel Pack | |
| Cycle | BI | Integrator | BI | Integrator |
| Complete Pre-vac, 132° C., 4 min. | Pass | Pass | Pass | Pass |
| Abort Pre-vac, 132° C., 3 pulses | Fail | Fail | Fail | Fail |
| Abort Pre-vac, 132° C., Abort at time = 0 min | Pass | Fail | Pass | Pass |
| Complete Gravity, 121° C., 30 min. | Pass | Pass | Pass | Pass |
| Abort Gravity, sterilize time = 7 min | Fail | Fail | Fail | Fail |
| Abort Gravity, sterilize time = 8 min | Marginal | Fail | Pass | Marginal |
| Abort Gravity, sterilize time = 15 min | Pass | Pass | Pass | Pass |

To be considered successful, each Test Pack configuration should provide the same result as for the 16-Towel Pack or fail somewhat more frequently than the 16-Towel Pack indicating performance equal to or slightly more stringent than the 16-Towel Test Pack.

As shown by the foregoing Examples, test packs in accordance with embodiments of the present invention provide reliable results, comparable to or better than those obtained by the standard 16-towel pack.

It is noted that, throughout the specification and claims, the numerical limits of the disclosed ranges and ratios may be combined, and are deemed to include all intervening values. Furthermore, all numerical values are deemed to be preceded by the modifier "about," whether or not this term is specifically stated.

While the principles of the invention have been explained in relation to certain particular embodiments, and are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A sterilization test pack, comprising:
    a base comprising a pair of recessed compartments, wherein the recessed compartments are arranged in a non-concentric relationship and are in fluid communication with each other, the base comprising a raised peripheral surface;
    a cover attached to the base and forming a sealed enclosure for the recessed compartments;
    at least one external channel formed in the raised peripheral surface of the base and providing the only fluid communication between the sealed enclosure and an external environment;
    a sterilization indicator in a first of the recessed compartments; and
    a chemical integrator, a chemical indicator, or both a chemical integrator and a chemical indicator in a second of the recessed compartments,
    wherein said external channel is configured to allow only restricted flow of a gaseous sterilization medium into the recessed compartments and the base and the cover are otherwise impenetrable by the gaseous sterilization medium,
    wherein the test pack is free of a sterilant absorber positioned within the sealed enclosure.

2. The sterilization test pack of claim 1 wherein the recessed compartments are in a substantially parallel side by side relationship.

3. The sterilization test pack of claim 1 comprising one said external channel, wherein the one external channel is in direct fluid communication with only the first of the recessed compartments, and the first recessed compartment is in fluid connection with the second of the recessed compartments via an internal channel.

4. The sterilization test pack of claim 1 comprising two said external channels, wherein a first of said two external channels is in fluid communication with the first of the recessed compartments, and a second of said two external channels is in fluid communication with the second of the recessed compartments.

5. The sterilization test pack of claim 4 wherein the first and second recessed compartments are in fluid communication with each other via an internal channel.

6. The sterilization test pack of claim 4 wherein each external channel comprises an S-shape channel having two bends.

7. The sterilization test pack of claim 4 wherein the sterilization indicator comprises a biological indicator.

8. The sterilization test pack of claim 1 wherein the external channel has at least one bend between the sealed enclosure and the external environment.

9. The sterilization test pack of claim 1 wherein each external channel independently has a depth in the range from about 0.025 mm to about 4 mm and a width in the range from about 0.025 mm to about 5 mm, and a length in the range from about 1 mm to about 100 mm.

10. The sterilization test pack of claim 9 wherein the depth and width of the external channel are selected to provide the restricted flow of the gaseous sterilization medium appropriate for the selected sterilization indicator.

11. The sterilization test pack of claim 1 wherein the sterilization indicator comprises at least one of a biological indicator and an indicator enzyme.

12. The sterilization test pack of claim 1 wherein at least one of the base or the cover is sufficiently transparent that the chemical indicator is visible after the sterilization test pack has been exposed to the sterilization medium.

13. The sterilization test pack of claim 1 wherein the base comprises one or a combination of two or more of polycarbonate, polyolefin, polystyrene, polyacrylamide, polymethacrylate, poly(methyl)methacrylate, polyimide, polyester, polyethylene terephthalate, polybutylene terephthalate and polyvinylchloride.

14. The sterilization test pack of claim 1 wherein the cover comprises one or a combination of two or more of mylar, metal foil, metallized foil, polyester, polyolefin, polycarbonate, polystyrene, polyacrylamide, polymethacrylate, poly(methyl)methacrylate, polyimide, polyester, polyethylene terephthalate, polybutylene terephthalate, polyvinylchloride and cardboard.

15. The sterilization test pack of claim 1 wherein the cover is sealed to the base by one or a combination of two or more of heat, adhesive, heat-activated laminate adhesion, sonic welding and magnetic induction.

16. The sterilization test pack of claim 1 wherein the base comprises a substantially flat raised surface to which the cover is sealed.

17. The sterilization test pack of claim 1 wherein the pair of compartments are in a substantially parallel and rectilinear relationship.

18. The sterilization test pack of claim 1 wherein the external channel is molded into the raised peripheral surface and is completed by the cover bridging over the external channel.

* * * * *